United States Patent
Abney et al.

(10) Patent No.: US 6,479,683 B1
(45) Date of Patent: Nov. 12, 2002

(54) PROCESS FOR CONJUGATING FATTY ACID ESTERS

(75) Inventors: Curt Abney, Sioux City, IA (US); John Anderson, Salix, IA (US)

(73) Assignee: Ag Processing Inc, Omaha, NE (US)

( * ) Notice: Subject to any disclaimer, the term of this patent is extended or adjusted under 35 U.S.C. 154(b) by 57 days.

(21) Appl. No.: 09/800,034

(22) Filed: Mar. 6, 2001

(51) Int. Cl.[7] .............................................. C07B 35/08

(52) U.S. Cl. ..................................... 554/126; 554/125

(58) Field of Search ................................. 554/126, 125

(56) References Cited

U.S. PATENT DOCUMENTS

| | | |
|---|---|---|
| 2,242,230 A | 5/1941 | Burr |
| 2,343,644 A | 3/1944 | Cawley |
| 2,350,583 A | 6/1944 | Bradley |
| 2,389,260 A | 11/1945 | Kirschenbauer |
| 3,162,658 A | 12/1964 | Baltes et al. |
| 3,278,567 A | 10/1966 | Rathjen et al. |
| 3,729,379 A | 4/1973 | Emken et al. |
| 3,984,444 A | 10/1976 | Ritz et al. |
| 4,164,505 A | 8/1979 | Krajca |
| 4,381,264 A | 4/1983 | Struve |
| 4,868,001 A | 9/1989 | Maruta |
| 5,017,614 A | 5/1991 | Pariza et al. |
| 5,070,104 A | 12/1991 | Pariza et al. |
| 5,208,356 A | 5/1993 | Pariza et al. |
| 5,288,619 A | 2/1994 | Brown et al. |
| 5,428,072 A | 6/1995 | Cook et al. |
| 5,430,066 A | 7/1995 | Cook et al. |
| 5,504,114 A | 4/1996 | Cook et al. |
| 5,554,646 A | 9/1996 | Cook et al. |
| 5,585,400 A | 12/1996 | Cook et al. |
| 5,674,901 A | 10/1997 | Cook et al. |
| 5,716,926 A | 2/1998 | Beale et al. |
| 5,725,873 A | 3/1998 | Cook et al. |
| 5,756,469 A | 5/1998 | Beale |
| 5,760,082 A | 6/1998 | Cook et al. |
| 5,760,083 A | 6/1998 | Cook et al. |
| 5,770,247 A | 6/1998 | Satter et al. |
| 5,804,210 A | 9/1998 | Cook et al. |
| 5,814,663 A | 9/1998 | Cook et al. |
| 5,827,885 A | 10/1998 | Cook et al. |
| 5,837,733 A | 11/1998 | Pariza et al. |
| 5,851,572 A | 12/1998 | Cook et al. |
| 5,855,917 A | 1/1999 | Cook et al. |
| 5,856,149 A | 1/1999 | Cook et al. |
| 5,892,074 A | 4/1999 | Seidel |
| 5,914,346 A | 6/1999 | Cook et al. |
| 5,919,451 A | 7/1999 | Cook et al. |
| 5,919,767 A | 7/1999 | Beale |
| 5,986,116 A | 11/1999 | Iwata et al. |
| 6,015,833 A | 1/2000 | Cook et al. |
| 6,019,990 A | 2/2000 | Remmereit |
| 6,020,376 A | 2/2000 | Pariza et al. |
| 6,020,377 A | 2/2000 | O'Quinn et al. |
| 6,020,378 A | 2/2000 | Cook et al. |
| 6,034,132 A | 3/2000 | Remmereit |
| 6,042,869 A | 3/2000 | Remmereit |

FOREIGN PATENT DOCUMENTS

| | | |
|---|---|---|
| EP | 0 597 901 A1 | 1/1994 |
| WO | WO 94/16690 | 8/1994 |

OTHER PUBLICATIONS

Chem. Abstr., Baltes et al., 55:96422, 1961.*
*Comprehensive Organic Transformations*, (1989), vol. 287, pp 110–114.
Shorland et al., (1957) *Biochem J.* "The Effect of Sheep–Rumen Contents on Unsaturated Fatty Acids," vol. 67, pp 328–333.
Gensler et al., (1951) *JACS, ISSN 0002–7863*, "Synthesis of Unsaturated Fatty Acids: Linoleic Acid," vol. 73, pp 4601–4604.
Hilditch, (1956), *The Chemical Constitution of Natural Fats*, (Chapman & Hall) London, 2nd ed.
*Official Methods and Recommended Practices of the American Oil Chemists' Society, 3rd Edition*, (1998), "Preparation of Methyl Esters of Long–Chain Fatty Acids."
Christle, et al., (1998), *JAOCS*, "Laboratory Preparation of Conjugated Linoleic Acids," vol. 75, No. 9, p 1227.
Wolff, (1993), *JAOCS*, "Further Studies on Artificial Geometrical Isomers of α–Linolenic Acid in Edible Linolenic Acid–Containing Oils," vol. 70, No. 3, pp 219–224.
*Biochemical Preparations*, (1955), vol. 4, pp 86–90.
Swern et al., (1953), *JAOCS*, "Application of Urea Complexes in the Purification of Fatty Acids, Esters, and Alcohols. III. Concentrates of Natural Linoleic and Linolenic Acids," vol. 30, pp 5–7.
McCutcheon, (1955), *Organic Synthesis Collective*, "Linoleic Acid," vol. 3, pp 526–531.
Nigam et al., (1956), *J. Chem.Soc.*, "Unsaturated Fatty Acids, Part II, The Synthesis of Linolenic Acid," pp 4049–4054.
Raphael et al., (1950), *J. Chem. Soc.*, The Synthesis of Long–chain Aliphatic Acids from Acetylenic Compounds. Part III. The Synthesis of Linoleic Acid, pp 2100–2103.
Walborsky, et al., (1951), *JACS*, "A Total Synthesis of Linoleic Acid," vol. 73, pp 2590–2594.
Osbond et al., (1959), *Chemistry and Industry*, "Synthesis of Linoleic, γ–Linolenic, Arachidonic and Docosa–4:7:10:16–Pentaenoic Acids," pp 1288–1292.

(List continued on next page.)

*Primary Examiner*—Deborah Carr
(74) *Attorney, Agent, or Firm*—McDonnell Boehnen Hulbert & Berghoff

(57) ABSTRACT

This invention relates to a process for producing conjugated fatty acid esters. More particularly, this invention relates to a process for producing conjugated fatty acid esters comprising subjecting one or a mixture of unconjugated fatty acid esters to a base-catalyzed isomerization reaction in the presence of only small amounts of catalyst and solvent in a closed vessel at an elevated temperature and under the corresponding autogenic pressure.

14 Claims, No Drawings

OTHER PUBLICATIONS

Hansen, (1986), *TIBS 11*, "The Essential Nature of Linoleic Acid in Mammals," pp 263–265.

Fritsche et al., (1998), *Fett/Lipid*, "Analysis, Occurrence, and Physiological Properties of Trans Fatty Acids (TFA) with Particular Emphasis on Conjugated Linoleic Acid Isomers (CLA)—A Review," vol. 100, pp 190–210.

Ma et al., (1999), *JAOCS*, "Preparation of Conjugated Linoleic Acid from Safflower Oil," vol. 76, No. 6, pp 729–730.

Berdeaux et al., (1998), *JAOCS*, "A Simple Method of Preparation of Methyl trans–10, cis–12 and cis–9, trans–11–Octadecadienoates from Methyl Linoleate," vol. 75, No. 12, pp 1749–1755.

*Official Methods and Recommended Practices of the American Oil Chemists' Society, 4th Edition*, (1990), "Poly–Unsaturated Acids."

Radlove et al., (1946), *Industrial and Engineering Chemistry*, "Catalytic Isomerization of Vegetable Oils," pp 997–1001.

Nichols et al, (1951), *J. Am. Chem. Soc.*, "Isomers of Conjugated Fatty Acids I. Alkali–isomerized Linoleic Acid," vol. 73, pp 247–252.

Gunstone, et al., (1976), *J. Sci. Fd Agric.*, "Improved Procedures for the Isolation of Pure Oleic, Linoleic, and Linolenic Acids or their Methyl Esters from Natural Sources," vol. 27, pp 675–680.

Chin, et al., (1994), *American Institute of Nutrition*, "Conjugated Linoleic Acid is a Growth Factor for Rats as Shown by Enhanced Weight Gain and Improved Feed Efficiency," pp 2344–2349.

Miller et al., (1994), *Biochemical and Biophysical Research Communications*, "Feeding Conjugated Linoleic Acid to Animals Partially Overcomes Catabolic Responses Due to Endotoxin Injection," vol. 198, No. 3, pp 1107–1112.

Mounts et al., (1970), *Lipids*, "Conjugation of Polyunsaturated Acids," vol. 5, No. 12, pp 997–1005.

Werner et al. (1992), *J. Agric. Food Chem.*, "Determination of Conjugated Linoleic Acid Content and Isomer Distribution in Three Cheddar–Type Cheeses: Effects of Cheese Cultures, Processing, and Aging," vol. 40, pp 1817–1821.

Hopkins, *Division of Chemistry, National Research Council of Canada, Ottawa, Canada*, "Fatty Acids with Conjugated Unsaturation," pp 37–87.

Glass, (1971), *Lipids*, "Alcoholysis, Saponification and the Preparation of Fatty Acid Methyl Esters," vol. 6, No. 12, pp 919–925.

Sehat et al., (1998), *Lipids*, "Identification of Conjugated Linoleic Acid Isomers in Cheese by Gas Chromatography, Silver Ion High Performance Liquid Chromatography and Mass Spectral Reconstructed Ion Profiles. Comparison of Chromatographic Elution Sequences," vol. 33, No. 10, pp 963–971.

Takagi et al., (1981), *Lipids*, "Occurrence of Mixtures of Geometrical Isomers of Conjugated Octadecatrienoic Acids in Some Seed Oils: Analysis by Open–Tubular Gas Liquid Chromatography and High Performance Liquid Chromatography," vol. 16, No. 7, pp 546–551.

Gunstone et al., (1971), *Lipids*, "Fatty Acids, Part 29 Methyl 12–Mesyloxyoleate as a Source of Cyclopropane Esters and of Conjugated Octadecadienoates," vol. 7, pp 121–134.

Ackman et al., (1974), *JAOCS*, "Linolenic Acid Artifacts from the Deodorization of Oils," vol. 51, pp 42–49.

Adlof, (1999), *Advances in Conjugated Linoleic Acid Research, vol. 1*, Chapter 3, "Preparation of Unlabeled and Isotope–Labeled Conjugated Linoleic and Related Fatty Acid Isomers," pp 21–38.

Yurawecz et al, (1999), *Advances in Conjugated Linoleic Acid Research, vol. 1*, Chapter 3, "Methylation Procedures for Conjugated Linoleic Acid," pp 64–82.

Park et al., (1999), *Abstract, INFORM*, "Comparison of Methylation Procedures for Conjugated Linoleic Acid (CLA)," vol. 10, No. 5, p 52.

\* cited by examiner

PROCESS FOR CONJUGATING FATTY ACID ESTERS

FIELD OF THE INVENTION

This invention relates to a process for producing conjugated fatty acid esters. More particularly, this invention relates to a process for producing conjugated fatty acid esters that comprises subjecting one or a mixture of unconjugated fatty acid esters to a base-catalyzed isomerization reaction in the presence of only small amounts of catalyst and solvent in a closed vessel at an elevated temperature and under the corresponding autogenic pressure.

BACKGROUND OF THE INVENTION

Fatty acids and fatty acid derivatives typically are derived from naturally occurring fats and oils. With few exceptions, such fatty acids or fatty acid derivatives are all straight-chain molecules having from three to eighteen carbon atoms. A significant fraction of these fatty acid molecules are polyunsaturated, meaning that they contain two or more double bonds. In most instances, the double bonds in naturally occurring polyunsaturated fatty acid molecules are separated from each other by two single bonds, with the structure —CH=CH—CH$_2$—CH=CH—, and such molecules are generally referred to as unconjugated polyenes or methylene-interrupted polyenes. In more limited instances, naturally occurring polyunsaturated fatty acid molecules contain double bonds separated from each other by a lone single bond, having the structure —CH=CH—CH=CH—, and such molecules are generally referred to as conjugated polyenes. Among the naturally occurring conjugated polyenes, conjugated dienes and trienes are the most prevalent.

Upon exposure to oxygen, conjugated polyenes oxidize relatively quickly and can form cross-linked films. Accordingly, conjugated polyenes traditionally have been valued by the paint and varnish industries for use in drying oils. Drying oils have value because of their ability to polymerize or "dry" after they have been applied to a surface to form tough, adherent and abrasion-resistant films. "Drying" of a paint or varnish does not simply entail evaporation of solvent, but rather a chemical reaction that produces a durable organic film, formed upon oxygen-induced polymerization and cross-linking of polyenes, analagous to the sulfur-induced polymerization and cross-linking that produces vulcanized rubber. Unconjugated polyenes, such as those contained in linseed oil and tung oil, also cross-link to form such fihns; however, conjugated polyenes cross-link more rapidly. Hence, drying oil formulations incorporating conjugated polyenes have quicker drying times than those formulations that incorporate only unconjugated polyenes.

In the area of health and nutrition, researchers have shown that ingestion of conjugated polyenes may inhibit tumor growth, prevent heart disease, and reduce body fat. Indeed, there is presently a great deal of interest in the apparent health benefits imparted by certain conjugated linoleic acids, termed CLAs. CLAs, originally isolated from the fat and milk of ruminants, exhibit impressive physiological effects in animal studies. CLA is a loose term used to describe one or a mixture of conjugated octadecadienoic fatty acids. In a variety of chemical forms, including but not limited to free fatty acids (FFA) and fatty acid methyl esters (FAME), CLA reportedly has antidiabetic properties, leads to reduced carcinogenesis and atherosclerosis, and increases bone and muscle mass.

A factor hampering commercialization and research interests in CLA and other conjugated polyenes, however, is that such compounds are not naturally abundant. Conjugated polyenes typically are present in animal fats only at a level of about 0.5 percent. In plant sources, conjugated polyenes do not occur widely. Although a small number of conjugated $C_{18}$ trienes are found to a certain extent in some seed oils, such as tung oil (china wood oil, *Aleurites fordii*, Euphorbiaceae), and some conjugated $C_{18}$ dienes are present in tall oil, a product obtained from pine wood during sulfate pulping processes, there are few natural plant sources of conjugated polyenes. Thus, investigators continue to seek ways to obtain conjugated polyenes in quantity by partial or total synthesis.

Several methods exist for preparing conjugated polyenes, including (1) biosynthesis; (2) dehydration of hydroxy fatty acids; and (3) isomerization. Biosynthetic methods have been used to prepare a number of conjugated dienes. The use of bacterial enzymes in such syntheses came about when researchers discovered that bacteria found in the stomachs of ruminants convert dietary unsaturated fatty acids contained in plant food sources into conjugated isomers. For example, the enzyme linoleate isomerase, isolated from the rumen anaerobic bacterium *Butyrivibrio fibrisolvens*, isomerizes linoleic acid to mainly cis-9, trans-11-octadecadienoic acid (c9, t11-18:2), which is sometimes referred to as rumenic acid. However, biosynthetic methods are not preferred for several reasons, including generally low yields and the difficulty of isolating specific conjugated compounds from the mixture that results.

In preparing conjugated polyenes via dehydration of hydroxy fatty acids, various isomers can be obtained. For example, dehydration of ricinoleic acid (12-hydroxy-9-cis-octadecenoic acid, also termed 12-hydroxy oleic acid) at 235° C. with activated alumina catalyst leads to 9-cis,11-trans-18:2. Dehydration of ricinelaidic (12-hydroxy-9-trans-octadecenoic acid) at 200° C. under vacuum with potassium acid sulfate catalyst leads to 9-trans, 11-trans-18:2. Dehydration of methyl ricinoleate where the hydroxy group is first converted to its mesyl (methanesulfonate) or tosyl (toluene-p-sulfonate) ester also has been investigated. For example, heating the mesyl ester of methyl ricinoleate at 100° C. with NaOCH$_3$/DMSO, DBU (1,5, -diazobicyclo(5.4.0)undec-5-ene), or DBN (1,5, -diazobicyclo(4.3.0)non-5-ene), leads to 9-cis,11-trans-18:2 conjugated ester. However, although these methods allow yields that are somewhat better than biosynthetic methods, yields seen in such dehydrogenation methods nevertheless are still less than about 70 percent. Moreover, dehydration of ricinoleates can produce conjugated compounds in which both double bonds have shifted relative to the starting compound. Due in part to these problems, these methods have not been widely utilized.

Synthesis of conjugated polyenes via isomerization typically proceeds from an unconjugated polyene fatty acid or fatty acid ester as precursor. Probably the most common unconjugated polyene precursor employed in such methods is linoleic acid. According to the delta ($\Delta$) nomenclature system, linoleic acid can be expressed as all-cis-9,12-octadecadienoic acid, or c9,c12-octadecadienoic acid, where c indicates the cis-configuration (the orientation that almost invariably occurs in linoleic acid derived from natural sources) and the numbers 9 and 12 indicate the position of the double bonds relative to the carboxyl carbon of the acyl chain (—COOH). This nomenclature can be abbreviated in several ways, including: 18:2 (Δ9,12); 18:2-c9,c12; 9-cis, 12-cis-18:2; and c9,c12-18:2, where c indicates the cis-configuration, 18 indicates the total number of carbon atoms, and 2 represents the number of double bonds in the molecule. Using alternative nomenclature, linoleic acid can be expressed in the (n-6) or omega (ω) system as 18:2 (n-6) or 18:2 ω6, where (n-6) or ω6 indicates the position of the first double bond beginning from the methyl end.

Isomerization produces various isomers that have the same atomic composition as the parent compound but that differ in chemical structure. The structural differences in isomers can be both positional and geometrical. Positional isomers result from the migration of double bonds. Geometric isomers result from the various combinations of cis and trans configurations such positional isomers can adopt. Thus, each positional isomer may occur as one or more of four possible geometric isomers. For example, isomerization of linoleic acid [18:2 (Δ9,12)] could produce a total of at least eight isomers: two positional isomers [18:2 (Δ9,11) and 18:2 (Δ10,12)], each of which could appear as four geometric isomers [(18:2-c9,c11; 18:2-c9,t11; 18:2-t9,c11; and 18:2-t9,t11); and (18:2-c10,c12; 18:2-c10,t12; 18:2 t10,c12; and 18:2-t10,t12), respectively].

Isomerization of unconjugated polyenes to produce conjugated polyenes can be accomplished in several ways, including (1) photochemically; (2) by means of metallic ion or metal carbonyl catalysts; (3) on treatment with acids; and (4) on treatment with strong bases. A typical photoisomerization process entails irradiating an unconjugated precursor with light of a suitable wavelength range in a solvent and optionally in the presence of a suitable photosensitizer. The source of light of the desired wavelength range is generally a xenon lamp or a medium- or high-pressure mercury vapor lamp. Disadvantages of this method include the need for special equipment and the need to remove residual photosensitizer from the final product. Moreover, yields obtained with photoisomerization typically are only about 80 percent.

Double-bond migrations can also take place by means of treatment with metallic ion (most often, complex compounds containing Pd, Pt, Rh, or Ru) or metal carbonyl catalysts. This type of isomerization proceeds according to one of two possible mechanisms. The first mechanism, known as the metal-hydride addition-elimination reaction, requires external hydrogen. The second mechanism, called the π-allyl complex mechanism does not require external hydrogen. In either case, however, the transition metals typically required in this type of isomerization are expensive and sometimes toxic.

Double-bond rearrangements can also take place on treatment with acids. This type of isomerization follows a two-step mechanism, where one of the doubly-bonded carbon atoms first gains a proton, giving a carbocation, and then the methylene unit adjacent to the other doubly-bonded carbon atom loses a proton, causing a double bond to reform. The most thermodynamically stable isomer is the one predominantly formed during isomerization. Acid-catalyzed isomerization is not a preferred method, however, because carbocations generate many side products in addition to the desired conjugated isomers.

Probably the most common isomerization methods used to produce conjugated polyenes involve treatment of unsaturated compounds with strong base. Such methods are sometimes termed alkali-catalyzed, base-catalyzed, or base-promoted isomerization. As in the case of the acid-catalyzed isomerization reaction, base-catalyzed isomerization produces equilibrium mixtures of the most thermodynamically stable isomers.

Base-catalyzed double bond isomerization, sometimes called prototropic rearrangement, is an example of electrophilic substitution with accompanying allylic rearrangement. Because the double bond of the unconjugated substrate can shift to be in conjugation with one already present, the double bond will migrate that way because the conjugated configuration is more thermodynamically stable. The reaction mechanism, illustrated in Scheme 1, involves abstraction of a hydrogen atom by the base to give resonance-stabilized carbanion species, represented by I and II of Scheme 1.

The relative ease of abstraction of hydrogen atoms follows the sequence allylic $>3°>2°>1>CH_4>$vinylic. Thus, a hydrogen atom attached to a double-bonded carbon, known in the art as a vinylic hydrogen, is harder to abstract than, say, a primary hydrogen. By contrast, a hydrogen atom attached to a carbon atom next to a double bond, known as an allylic hydrogen, is even easier to abstract than a tertiary hydrogen.

As illustrated in Scheme 2, following abstraction of hydrogen, the acid $BH^+$ then protonates the carbanion species at the position that will give the more stable compound. The ratio of the possible isomerization products can vary with the identity of $BH^+$.

Base-catalyzed double-bond shifts are generally intramolecular. The intramolecularity has been hypothesized to follow a "conducted tour mechanism," illustrated in Scheme 3, in which the base leads a proton from one carbanionic site to the other.

Various methods exist for producing conjugated polyenes via base-catalyzed isomerization of an unconjugated substrate; however, each of these prior methods has certain drawbacks. In one known method, isomerization occurs upon treatment of a substrate with an excess of alkali metal hydroxide in an aqueous or hydroxylated solvent medium. For example, as illustrated in A.O.C.S. Official Method Cd 7-58, conjugated compounds are obtained by adding a solution of potassium hydroxide in ethylene glycol to an unconjugated substrate in a weight ratio of about 110:1 and maintaining the reaction at 180° C. for 25 minutes. However, this process employs a considerable excess of alkali metal hydroxide catalyst, adding expense and presenting safety concerns.

In another example of an aqueous isomerization process that requires considerable excess alkali, U.S. Pat. No. 2,230,583 discloses a conjugation process that comprises heating an aqueous solution of soaps of unconjugated fatty acids with excess aqueous alkali in a pressure vessel at a temperature of from 200–230° C. and under autogenic pressure. However, using such high temperatures induces formation of undesirable trans,trans isomers. Moreover, this process only converts about 50 percent of the dienes to their conjugated form.

Scheme 1

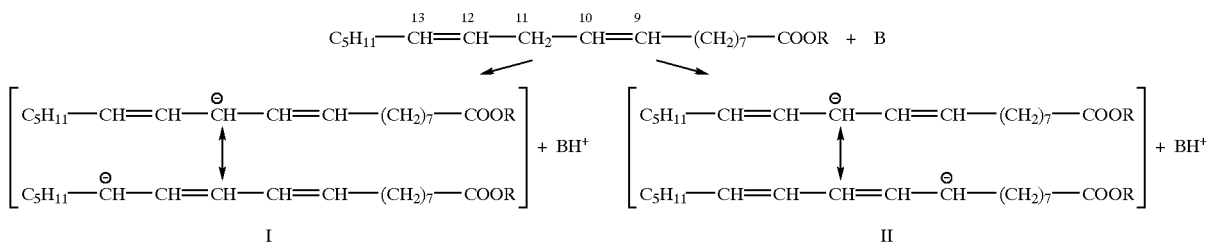

Scheme 2

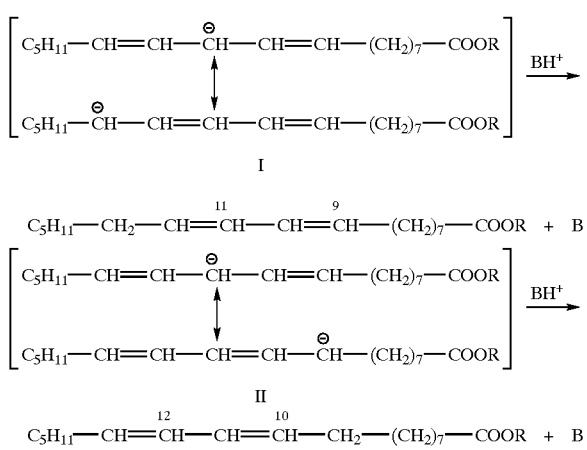

In one known non-aqueous isomerization process, U.S. Pat. No. 2,242,230 iscloses a process that involves treating an unconjugated fatty acid compound with a basic eagent catalyst such as an alkali alcoholate in a considerable excess of non-aqueous solvent at an elevated temperature. A drawback to this method is that it requires use of an amount of solvent several times the weight of the substrate treated, thereby presenting the need for additional processing steps to separate the conjugated product from the solvent. Another drawback to this method is that lengthy reaction times, sometimes as much as 24 hours, are required.

In yet another known non-aqueous isomerization process, U.S. Pat. No. 3,162,658 discloses a process that comprises treating unconjugated fatty acid esters with no more than a stoichiometric amount of an alkali alcoholate at a temperature in the range of 100° C. to 140° C. and preferably in the presence of an inert solvent. One drawback of this method is that under such reaction conditions, short chain monohydric solvents such as methanol and ethanol evaporate rapidly and no longer facilitate uniform contact between the unconjugated substrate and the basic reagent. Hence, when the solvent is a monohydric alcohol, higher-boiling branched $C_3$ or $C_4$ alcohols such as isopropanol, sec-butanol, or tert-butanol generally must be employed. Another drawback to this method is that a reaction time of up to 5 hours is required to achieve nearly complete conversion of unconjugated substrate into conjugated reaction products.

Thus, problems remain, and investigators continue to seek more efficient isomerization methods. The present invention Scheme 3

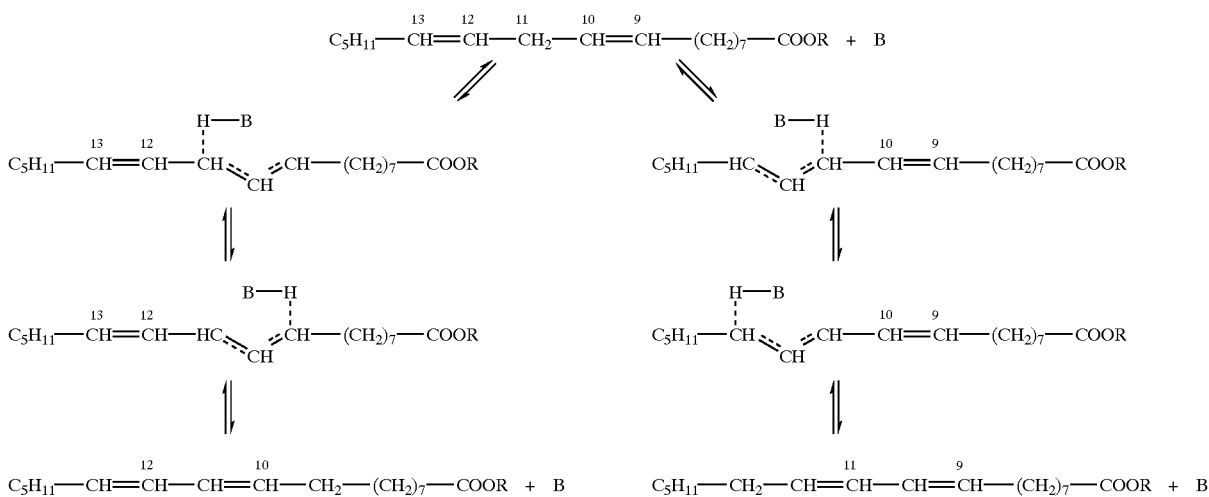

has advantages over those previously disclosed. In particular, this invention relates to an improved process for producing conjugated fatty acid esters that comprises subjecting one or a mixture of unconjugated fatty acid esters to a base-catalyzed isomerization reaction in the presence of only small amounts of catalyst and solvent in a closed vessel at an elevated temperature and under the corresponding autogenic pressure.

SUMMARY OF THE INVENTION

One aspect of the present invention relates to an improved process for producing conjugated fatty acid esters using one or more fatty acid esters as substrate.

Another aspect of the invention relates to an improved process for producing conjugated fatty acid esters using only small amounts of catalyst and solvent.

One embodiment of the invention is a process for producing conjugated fatty acid esters that comprises providing a substrate containing at least one unconjugated polyene fatty acid ester; forming a reaction mixture by combining the substrate with from about 1 to about 5 percent by weight of an alkali metal alkoxide catalyst and from about 1 to about 5 percent by weight of a monohydric alcohol solvent, wherein the ratio of catalyst to solvent is from about 1:0.5 to about 1:3; and subjecting the reaction mixture to a base-catalyzed isomerization reaction in a closed vessel at a temperature of from about 275 to about 350° F. and under the corresponding autogenic pressure for a time sufficient to generate a reaction product containing conjugated fatty acid methyl esters and potassium salts of conjugated fatty acids, in which at least about 90 percent of the unconjugated polyene fatty acid esters have been converted into conjugated forms.

Another embodiment of the invention is a process for producing conjugated fatty acid esters that comprises providing a substrate containing at least one unconjugated polyene fatty acid ester; combining the substrate with from about 1 to about 5 percent by weight of an alkali metal alkoxide catalyst to form a premix; combining the premix with from about 1 to about 5 percent by weight of a monohydric alcohol solvent to form a reaction mixture containing catalyst and solvent in a ratio of from about 1:0.5 to about 1:3; and subjecting the reaction mixture to a base-catalyzed isomerization reaction in a closed vessel at a temperature of from about 275 to about 350° F. and under the corresponding autogenic pressure for a time sufficient to generate a reaction product containing conjugated fatty acid methyl esters and potassium salts of conjugated fatty acids, in which at least about 90 percent of the unconjugated polyene fatty acid esters have been converted into conjugated forms.

A further embodiment of the invention is a process for producing conjugated fatty acid esters that comprises providing a substrate containing at least one unconjugated polyene fatty acid ester; combining from about 1 to about 5 percent by weight of an alkali metal alkoxide catalyst and from about 1 to about 5 percent by weight of a monohydric alcohol solvent to form a catalyst solution having a catalyst to solvent ratio of from about 1:0.5 to about 1:3; combining the catalyst solution and the substrate to form a reaction mixture; and subjecting the reaction mixture to a base-catalyzed isomerization reaction in a closed vessel at a temperature of from about 275 to about 350° F. and under the corresponding autogenic pressure for a time sufficient to generate a reaction product containing conjugated fatty acid methyl esters and potassium salts of conjugated fatty acids, in which at least about 90 percent of the unconjugated polyene fatty acid esters have been converted into conjugated forms.

A still further embodiment of the invention is a process for producing conjugated fatty acid esters that comprises providing a substrate containing at least one unconjugated polyene fatty acid ester; forming a reaction mixture by combining the substrate with from about 1 to about 5 percent by weight of an alkali metal alkoxide catalyst and from about 1 to about 5 percent by weight of a monohydric alcohol solvent, wherein the ratio of catalyst to solvent is from about 1:0.5 to about 1:3; subjecting the reaction mixture to a base-catalyzed isomerization reaction in a closed vessel at a temperature of from about 275 to about 350° F. and under the corresponding autogenic pressure for a time sufficient to generate a reaction product containing conjugated fatty acid methyl esters and potassium salts of conjugated fatty acids, in which at least about 90 percent of the unconjugated polyene fatty acid esters have been converted into conjugated forms; combining the reaction product with water to produce an oil phase containing the conjugated fatty acid methyl esters and a water phase containing the potassium salts of conjugated fatty acids; separating the oil phase and the water phase; and combining the water phase with a 98% aqueous sulfuric acid solution in an amount of from about 1 to about 20 percent by weight to convert the potassium salts of conjugated fatty acids into conjugated free fatty acids.

A yet further embodiment of the invention is a process for producing conjugated fatty acid esters that comprises providing a substrate containing at least one unconjugated polyene fatty acid ester; forming a reaction mixture by combining the substrate with from about 1 to about 5 percent by weight of an alkali metal alkoxide catalyst and from about 1 to about 5 percent by weight of a monohydric alcohol solvent, wherein the ratio of catalyst to solvent is from about 1:0.5 to about 1:3; subjecting the reaction mixture to a base-catalyzed isomerization reaction in a closed vessel at a temperature of from about 250 to about 375° F. and under the corresponding autogenic pressure for a time sufficient to generate a reaction product containing conjugated fatty acid methyl esters and potassium salts of conjugated fatty acids, in which at least about 90 percent of the unconjugated polyene fatty acid esters have been converted into conjugated forms; combining the reaction product with a 98% aqueous sulfuric acid solution in an amount of from about 1 to about 20 percent by weight to convert the potassium salts of conjugated fatty acids into conjugated free fatty acids; and separating the conjugated fatty acid methyl esters and the conjugated free fatty acids.

An even further embodiment of the invention is a process for producing conjugated fatty acid esters that comprises providing a substrate containing at least one unconjugated polyene fatty acid ester; forming a reaction mixture by combining the substrate with from about 1 to about 5 percent by weight of an alkali metal alkoxide catalyst and from about 1 to about 5 percent by weight of a monohydric alcohol solvent, wherein the ratio of catalyst to solvent is from about 1:0.5 to about 1:3; subjecting the reaction mixture to a base-catalyzed isomerization reaction in a closed vessel at a temperature of from about 250 to about 375° F. and under the corresponding autogenic pressure for a time sufficient to generate a reaction product containing conjugated fatty acid methyl esters and potassium salts of conjugated fatty acids, in which at least about 90 percent of the unconjugated polyene fatty acid esters have been converted into conjugated forms; combining the reaction product with a 98% aqueous sulfuric acid solution in an amount of from about 1 to about 20 percent by weight to convert the potassium salts of conjugated fatty acids into conjugated free fatty acids; and methylating the conjugated free fatty acids to generate a product that comprises greater than about 95 percent by weight conjugated fatty acid methyl esters.

These and other aspects and embodiments of the invention will become apparent in light of the detailed description below.

DESCRIPTION OF A PREFERRED EMBODIMENT

In the present invention, a substrate containing at least one unconjugated polyene fatty acid ester is subjected to an isomerization reaction catalyzed by small amounts of an alkali metal alkoxide catalyst and a monohydric alcohol solvent in a closed vessel at an elevated temperature and under the corresponding autogenic pressure. The improved processes of the invention for producing conjugated polyene fatty acid esters can be conducted as batch, semi-continuous, or continuous processes. The term unconjugated polyene fatty acid ester means an ester derivative of a fatty acid compound having methylene-interrupted double bonds.

Substrates suitable for use in the present invention are natural or synthetic sources containing unconjugated polyene fatty acid esters including but not limited to alkyl esters of linoleic acid (9,12-octadecadienoic acid) and linolenic acid (9,12,15-octadecatrienoic acid). Generally, the substrate should contain at least about 45 percent by weight unconjugated polyene fatty acid esters.

Naturally-derived substrates are conveniently obtained during the refining of oils derived from linoleic acid-containing natural plant sources. Table 1 summarizes several natural sources that generate oils rich in linoleic acid.

TABLE 1

| Source | % Linoleic Acid | % Linolenic Acid |
| --- | --- | --- |
| Poppy | 77 | 0 |
| Safflower | 75 | 0 |
| Linola flaxseed | 72 | 3 |
| Cucumber | 72 | 0 |
| Grapeseed | 70 | 0 |
| Sunflower | 69 | 0 |
| Walnut | 62 | 12 |
| Pumpkin | 60 | 0 |
| Corn | 57 | 0 |
| Soybean | 53 | 8 |
| Cottonseed | 53 | 0 |
| Peanut | 41 | trace |
| Sesame | 45 | 1 |

Based on ease of commercial availability, a preferred naturally-derived substrate is a material derived from soybean or sunflower oil and which contains methyl or ethyl esters of linoleic and linolenic acid. Most preferably, the naturally-derived substrate is a material termed soy methyl ester, comprising methyl esters of linoleic and linolenic acid, or is a material termed sunflower methyl ester, comprising methyl esters of linoleic acid. Soy methyl esters and sunflower methyl esters are obtained by reacting the appropriate source oil (soy or sunflower) with a reactant and a catalyst at a temperature of about 150° F. to form glycerin, soap, and methyl ester. The methyl ester is then separated and dried at a temperature of about 230° F. to remove residual water and reactant. Drying conveniently occurs in the reactor due to its internal steam coils. The typical composition of soy methyl esters is 11% 16:0, 4% 18:0, 22% 18:1, 53% 18:2, 8% 18:3, and 2% other compounds. The typical composition of sunflower methyl esters is 6% 16:0, 5% 18:0, 20% 18:1, 69% 18:2, and trace amounts of 18:3.

The invention can also be practiced using a substrate comprised wholly or in part of synthetic sources of unconjugated polyene fatty acid esters. For example, the substrate can comprise ester derivatives of synthetically prepared linoleic acid. One classical method for preparing linoleic acid comprises brominating a linoleic acid-rich mixture of fatty acids, followed by debromination with zinc in methanol or other solvents.

After the substrate is provided, a reaction mixture is formed by combining the substrate with from about 1 to about 5 percent by weight of an alkali metal alkoxide catalyst and from about 1 to about 5 percent by weight of a monohydric alcohol solvent, wherein the ratio of catalyst to solvent is from about 1:0.5 to about 1:3. The reaction mixture can be formed by combining all ingredients simultaneously or in any order. The reaction mixture can also be formed by combining two ingredients and then combining the resulting product and the third ingredient. For example, the reaction mixture can be formed by combining the catalyst and the substrate to form a premix, and then combining the premix and the solvent. The reaction mixture can also be formed by combining the catalyst and the solvent to form a catalyst solution, and then combining the catalyst solution and the substrate.

Suitable alkali metal alkoxide catalysts include alkali metal methoxides and ethoxides, where the alkali metal comprises potassium, sodium, or lithium. Preferably, the catalyst is potassium methoxide or sodium methoxide. Most preferably, the catalyst is potassium methoxide. The catalyst can be used in powdered or solution form. The alkali metal alkoxide catalyst can be prepared in solution by dissolving fresh clean alkali metal in a monhydric alcohol. For example, a 30 wt % solution of sodium methoxide in methanol can be prepared by dissolving sodium in dry methanol. Potassium methoxide is an even better catalyst; however, care must be taken in preparing a potassium methoxide solution in the manner just described, because potassium can react very vigorously with methanol.

The catalyst is generally present at a level of from about 1 to about 5 percent by weight. More preferably, the level of catalyst is from about 2 to about 5 percent by weight. Most preferably, the level of catalyst is from about 2.5 to about 3.5 percent by weight. Within these ranges, the catalyst level is selected so that the catalyst to solvent ratio is from about 1:0.5 to about 1:3.

Suitable monohydric alcohol solvents include branched and straight chain $C_1$-$C_4$ alcohols. Preferably, the monohydric alcohol solvent is methanol, ethanol, or n-propanol. Most preferably, the monohydric alcohol solvent is methanol. The solvent facilitates uniform contact between the unconjugated substrate and the alkali metal alkoxide catalyst. The solvent can also facilitate ease of handling of raw materials by solubilizing the alkali metal alkoxide catalyst. Shorter chain monohydric alcohol solvents are preferred because any residual amounts contained in the conjugated polyene fatty acid ester reaction product can be easily removed. Monohydric alcohol solvents in general are preferred because they are less toxic than other solvents used in prior base-catalyzed isomerization processes, such as ethylene glycol.

The solvent is generally present at a level of from about 1 to about 5 percent by weight. More preferably, the level of solvent is from about 2 to about 4 percent by weight. Most preferably, the level of solvent is from about 2.5 to about 3.5 percent by weight. Within these ranges, the solvent level is selected so that the catalyst to solvent ratio is from about 1:0.5 to about 1:3.

The reaction mixture is then subjected to a base-catalyzed isomerization reaction in a closed vessel at a temperature of from about 275 to about 350° F. and under the corresponding autogenic pressure for a time sufficient to generate a reaction product containing conjugated fatty acid methyl esters and potassium salts of conjugated fatty acids, in which at least about 90 percent of the unconjugated polyene fatty acid esters have been converted into conjugated forms. Preferably, the reaction mixture is kept agitated during the isomerization reaction. Also, because the conjugated polyenes that form during the isomerization reaction are susceptible to oxidative degradation, the reaction is best run under nitrogen blanketing or otherwise non-oxidizing conditions.

Generally, the isomerization reaction occurs at a temperature of from about 140 to about 170° C., preferably from about 150 to about 160° C., and most preferably from about 155 to about 160° C. Higher temperatures are not desirable due to the likelihood of converting conjugated isomers into undesirable trans,trans forms. The reaction temperature is selected to ensure that at least a portion of the solvent remains in solution at the corresponding autogenic pressure.

Keeping a portion of the solvent in solution facilitates agitation of the reaction mixture during isomerization, which can otherwise prove difficult since the onset of isomerization produces a dramatic increase in the viscosity of the reaction mixture. Keeping a portion of the solvent in solution also reduces the extent of catalyst inactivation that might otherwise occur if the alkali metal alkoxide were to participate in a saponification reaction with the fatty acid esters, rather than participating in the isomerization reaction.

The closed vessel in which the isomerization reaction is conducted can be of any convenient size and construction. Generally, the closed vessel comprises a thermally jacketed closed cylindrical vessel having one or more inlets, one or more outlets, and an internal mixing element. Preferably, the closed vessel is a stainless steel or glass-lined pressure reactor, such as a Parr Model 4522 pressure reactor available from Parr Instrument Co., Moline, Ill.

In addition to the autogenic pressure produced at the reaction conditions, pressure can also be augmented by an external pressure source. For example, to further increase pressure within the pressure reactor, an inert gas, particularly nitrogen, can be introduced into the vessel.

Conducting the isomerization reaction under autogenic pressure provides several benefits. First, use of pressure dramatically reduces the time required to convert unconjugated polyenes into conjugated forms by allowing use of higher reaction temperatures. Whereas prior known base-catalyzed isomerization methods require in some cases 24 hours to achieve conversion rates greater than 95 percent, the processes of the present invention requires less than about three hours, and often less than about 90 minutes, to achieve the same conversion rates.

Another benefit associated with conducting the isomerization reaction under pressure is that it enables the monohydric alcohol solvent to remain in solution at higher temperatures. Generally, as temperature increases, the rate of isomerization increases. However, higher temperatures promote volatilization of lower-boiling solvents, especially if the isomerization reaction is conducted under only ambient pressure. Thus, prior to this invention, lower-boiling solvents such as methanol were generally seldom employed, and where they were utilized, operators could not simultaneously attain optimal isomerization temperatures and keep the solvent in solution.

As stated above, keeping the solvent in liquid form promotes uniform contact between the substrate and the catalyst and thereby promotes rapid isomerization. Keeping the solvent in solution also promotes handling and energy efficiencies. Normally, as the reaction mixture begins to isomerize, there is an associated significant increase in viscosity that can make it more difficult to maintain uniform contact between the substrate and the catalyst, and which can lead to slower isomerization rates. This problem of viscosity increase is worsened when the solvent volatilizes at the reaction conditions. Keeping the solvent in liquid form reduces the chances and magnitude of swings in viscosity. Maintaining a more constant viscosity by keeping the solvent in liquid form also lessens or eliminates amperage fluctuations on mixing motors, and leads to less energy requirements overall.

The catalyst and solvent can be added prior to, during, or after heating of the substrate to the desired reaction temperature. Preferably, the catalyst and solvent are pre-mixed and added as a mixture.

The isomerization process of the invention produces a reaction product containing conjugated fatty acid methyl esters and potassium salts of conjugated fatty acids, in which at least about 95 percent of the unconjugated polyene fatty acid esters have been converted into conjugated forms. Generally, the reaction product contains conjugated fatty acid methyl esters and potassium salts of conjugated fatty acids in a ratio of about 10:1.

Several options exist for treating the reaction product further. For example, the reaction product can be combined with water to produce an oil phase containing the conjugated fatty acid methyl esters and a water phase containing the potassium salts of conjugated fatty acids. The water phase can then be separated and treated with a 98% aqueous sulfuric acid solution in an amount of from about 1 to about 20 percent by weight to convert the potassium salts of conjugated fatty acids into conjugated free fatty acids. Both the conjugated fatty acid methyl esters and the conjugated free fatty acids can then be dried under a vacuum of greater than about 24 inches of Hg and a temperature of about 110° C. until any residual water content is less than about 0.5 percent by weight.

Alternatively, the reaction product can be combined with a 98% aqueous sulfuric acid solution in an amount of from about 1 to about 20 percent by weight to convert the potassium salts of conjugated fatty acids into conjugated free fatty acids. The resulting product can then be dried under a vacuum of greater than about 24 inches of Hg and a temperature of about 110° C. until any residual water content is less than about 0.5 percent by weight. Optionally, the conjugated fatty acid methyl esters can then be separated from the conjugated free fatty acids.

In yet another alternative, the reaction product can be combined with a 98% aqueous sulfuric acid solution in an amount of from about 1 to about 20 percent by weight to convert the potassium salts of conjugated fatty acids into conjugated free fatty acids. A methylating agent can then be added to the mixture to methylate the conjugated free fatty acids to generate a product comprising greater than about 95 percent by weight conjugated fatty acid methyl esters, which can then be dried according to the procedure outlined above. Suitable methylating agents include but are not limited to dimethyl carbonate, methyl formate, methyl acetate, dimethyl sulfoxide, dimethyl sulfide, trimethyl borate, and nitromethane.

All documents, e.g., patents, journal articles, and textbooks, cited above or below are hereby incorporated by reference in their entirety.

One skilled in the art will recognize that modifications may be made in the present invention without deviating from the spirit or scope of the invention. The invention is illustrated further by the following examples, which are not to be construed as limiting the invention in spirit or scope to the specific procedures or compositions described therein.

EXAMPLE 1

A two-liter pressure reactor was charged with 750 grams of soy methyl ester containing 53% linoleic fatty acid methyl ester and 8% linolenic fatty acid methyl ester, and a nitrogen purge was started. Agitation was started, and the soy methyl ester was then heated to 50° C., following which 22.5 grams of potassium methoxide was added in solid form. Methanol was then added in amount of 30 grams, and the reactor contents were heated to 65° C. Nitrogen purge was then discontinued, and the reactor was sealed. The reactor contents were then heated to 150° C. and held at that temperature with agitation for one hour. Pressure within the reactor was 60 psi. The reaction product was then cooled and an analysis revealed that 93.5 percent of the conjugatable material (the linoleic and linolenic fatty acid methyl esters) had been converted into conjugated forms.

EXAMPLE 2

A two-liter pressure reactor was charged with 750 grams of soy methyl ester containing 53% linoleic fatty acid methyl ester and 8% linolenic fatty acid methyl ester, and a nitrogen purge was started. Agitation was started, and the soy methyl ester was then heated to 50° C., following which 22.5 grams of potassium methoxide was added in solid form. Methanol was then added in amount of 30 grams, and the reactor contents were heated to 65° C. Nitrogen purge was then discontinued, and the reactor was sealed. The reactor contents were then heated to 150° C. and held at that temperature with agitation for two hours. Pressure within the reactor was 60 psi. The reaction product was then cooled and an analysis revealed that 93.5 percent of the conjugatable material (the linoleic and linolenic fatty acid methyl esters) had been converted into conjugated forms.

EXAMPLE 3

A two-liter pressure reactor was charged with 1000 grams of soy methyl ester containing 53% linoleic fatty acid methyl ester, 8% linolenic fatty acid methyl ester, and 0.226 percent glycerin, and a nitrogen purge was started. Agitation was started, and the soy methyl ester was then heated to 50° C., following which potassium methoxide in solid form was added in an amount of 3 percent by weight of the soy methyl ester. Methanol was then added in amount of 3 percent by weight of the soy methyl ester, and the reactor contents were heated to 65° C. Nitrogen purge was then discontinued, and the reactor was sealed. The reactor contents were then heated to 150° C. and held at that temperature with agitation for one hour. Pressure within the reactor was 60 psi. The reaction product was then cooled and an analysis revealed that 94 percent of the conjugatable material had been converted into conjugated forms.

EXAMPLE 4

A two-liter pressure reactor was charged with 1000 grams of soy methyl ester containing 53% linoleic fatty acid methyl ester, 8% linolenic fatty acid methyl ester, and 0.226 percent glycerin, and a nitrogen purge was started. Agitation was started, and the soy methyl ester was then heated to 50° C., following which potassium methoxide in solid form was added in an amount of 3 percent by weight of the soy methyl ester. Methanol was then added in amount of 3 percent by weight of the soy methyl ester, and the reactor contents were heated to 65° C. Nitrogen purge was then discontinued, and the reactor was sealed. The reactor contents were then heated to 160° C. and held at that temperature with agitation for one hour. Pressure within the reactor was 60 psi. The reaction product was then cooled and an analysis revealed that 99 percent of the conjugatable material had been converted into conjugated forms.

EXAMPLE 5

A two-liter pressure reactor was charged with 1000 grams of soy methyl ester containing 53% linoleic fatty acid methyl ester, 8% linolenic fatty acid methyl ester, and 0.226 percent glycerin, and a nitrogen purge was started. Agitation was started, and the soy methyl ester was then heated to 50° C., following which solid form potassium methoxide was added in an amount of 2 percent by weight of the soy methyl ester. Methanol was then added in amount of 2 percent by weight of the soy methyl ester, and the reactor contents were heated to 65° C. Nitrogen purge was then discontinued, and the reactor was sealed. The reactor contents were then heated to 160° C. and held at that temperature with agitation for one hour. Pressure within the reactor was 60 psi. The reaction product was then cooled and an analysis revealed that 94 percent of the conjugatable material had been converted into conjugated forms.

EXAMPLE 6

A two-liter pressure reactor was charged with 1000 grams of sunflower methyl ester containing 69% linoleic fatty acid methyl ester and 0.13 percent glycerin, and a nitrogen purge was started. Agitation was started, and the sunflower methyl ester was then heated to 50° C., following which potassium methoxide in solid form was added in an amount of 3 percent by weight of the sunflower methyl ester. Methanol was then added in amount of 3 percent by weight of the sunflower methyl ester, and the reactor contents were heated to 65° C. Nitrogen purge was then discontinued, and the reactor was sealed. The reactor contents were then heated to 160° C. and held at that temperature with agitation for one hour. Pressure within the reactor was 60 psi. The reaction product was then cooled and an analysis revealed that 99 percent of the conjugatable material had been converted into conjugated forms.

EXAMPLE 7

Two reaction products obtained from soy methyl ester, and one reaction product obtained from sunflower methyl ester, wherein the percent of conjugatable material converted into conjugated forms was, respectively, 93.8%, 98.1%, and 97.6%, were analyzed to determine their content of various conjugated isomers, and the results are shown in Table 2.

TABLE 2

|  | Non-conjugated Isomers (wt %) | | | | | | Conjugated Isomers (wt %) | | | |
| --- | --- | --- | --- | --- | --- | --- | --- | --- | --- | --- |
|  | 16:0 | 18:0 | 18:1 | 18:2 | 18:3 | Other | 9c–11t | 10t–12c | 9c–11c | 9t–11t |
| Soybean Methyl Ester | 11.00 | 4.00 | 22.00 | 53.00 | 8.00 | 2.00 | — | — | — | — |
| 93.8% conjugated soy methyl ester | 10.30 | 4.50 | 20.22 | 3.92 | — | — | 26.77 | 29.14 | 0.97 | 4.14 |
| 98.1% conjugated soy methyl ester | 10.27 | 4.53 | 20.13 | 1.13 | 0.05 | — | 27.93 | 30.77 | 1.07 | 3.95 |

TABLE 2-continued

| | Non-conjugated Isomers (wt %) | | | | | | Conjugated Isomers (wt %) | | | |
|---|---|---|---|---|---|---|---|---|---|---|
| | 16:0 | 18:0 | 18:1 | 18:2 | 18:3 | Other | 9c–11t | 10t–12c | 9c–11c | 9t–11t |
| Sunflower Oil Methyl Ester | 6.00 | 5.00 | 20.00 | 69.00 | trace | — | — | — | — | — |
| 97.6% conjugated sun methyl ester | 5.71 | 3.93 | 20.21 | 1.66 | — | — | 31.27 | 34.20 | 1.01 | 2.01 |

The analyses in Table2 show that the isomerization process of the invention produces more 10t, 12c isomer than 9c, 11t isomer.

EXAMPLE 8

The reaction products of Example 7 were each acidulated with a 98% aqueous sulfuric acid solution in an amount of about 5 percent by weight in order to convert the potassium salts of conjugated fatty acids into conjugated free fatty acids. The acidulated reaction products were then analyzed to determine the relative amounts of conjugated methyl ester and conjugated free fatty acid, and the results are shown in Table 3.

TABLE 3

| | Methyl Ester (wt %) | Free Fatty Acid (wt %) |
|---|---|---|
| Soybean Oil Methyl Ester | 99.60 | 0.04 |
| 93.8% Conjugated Soy Methyl Ester | 86.90 | 7.70 |
| 98.1% Conjugated Soy Methyl Ester | 86.80 | 9.40 |
| 97.6% Conjugated Sunflower Methyl Ester | 90.20 | 10.40 |

As shown in Table 3, the isomerization process of the invention generally produces conjugated methyl ester and conjugated fatty acids in a ratio of from about 5:1 to about 15:1.

The invention and the manner and process of making and using it, are now described in such full, clear, concise and exact terms as to enable any person skilled in the art to which it pertains, to make and use the same. Although the foregoing describes preferred embodiments of the present invention, modifications may be made therein without departing from the spirit or scope of the present invention as set forth in the claims. To particularly point out and distinctly claim the subject matter regarded as invention, the following claims conclude this specification.

What we claim is:

1. A process for producing conjugated fatty acid esters, comprising:
   (a) providing a substrate containing at least one unconjugated polyene fatty acid ester;
   (b) forming a reaction mixture by combining the substrate with from about 1 to about 5 percent by weight of an alkali metal alkoxide catalyst and from about 1 to about 5 percent by weight of a monohydric alcohol solvent, wherein the ratio of catalyst to solvent is from about 1:0.5 to about 1:3; and
   (c) subjecting the reaction mixture to a base-catalyzed isomerization reaction in a closed vessel at a temperature of from about 275 to about 350° F. and under the corresponding autogenic pressure for a time sufficient to generate a reaction product containing conjugated fatty acid methyl esters and potassium salts of conjugated fatty acids, in which at least about 90 percent of the unconjugated polyene fatty acid esters have been converted into conjugated forms.

2. The process of claim 1, wherein step (b) combining comprises the steps of:
   (i) combining the catalyst and the substrate to form a premix; and
   (ii) combining the premix and the solvent.

3. The process of claim 1, wherein step (b) combining comprises the steps of:
   (i) combining the catalyst and the solvent to form a catalyst solution; and
   (ii) combining the substrate and the catalyst solution.

4. The process of claim 1, wherein the alkali metal alkoxide catalyst is selected from the group consisting of potassium methoxide, potassium ethoxide, sodium methoxide, sodium ethoxide, and mixtures thereof.

5. The process of claim 1, wherein the alkali metal alkoxide catalyst is potassium methoxide.

6. The process of claim 1, wherein the monohydric alcohol solvent is selected from the group consisting of methanol, ethanol, n-propanol, and mixtures thereof.

7. The process of claim 6, wherein the monohydric alcohol solvent is methanol.

8. The process of claim 1, wherein the substrate is selected from the group consisting of soybean oil methyl esters, sunflower oil methyl esters, and mixtures thereof.

9. The process of claim 1, wherein the isomerization reaction occurs at a temperature of from about 300 to about 350° F.

10. The process of claim 9, wherein the catalyst is potassium methoxide and the solvent is methanol.

11. The process of claim 1, wherein step (c) reaction time is less than about 2 hours.

12. The process of claim 1, further comprising the steps
   (d) combining the reaction product with water to produce an oil phase containing the conjugated fatty acid methyl esters and a water phase containing the potassium salts of conjugated fatty acids;
   (e) separating the oil phase and the water phase; and
   (f) combining the water phase with a 98% aqueous sulfuric acid solution in an amount of from about 1 to about 20 percent by weight to convert the potassium salts of conjugated fatty acids into conjugated free fatty acids.

13. The process of claim 1, further comprising the steps
   (d) combining the reaction product with a 98% aqueous sulfuric acid solution in an amount of from about 1 to about 20 percent by weight to convert the potassium salts of conjugated fatty acids into conjugated free fatty acids; and
   (e) separating the conjugated fatty acid methyl esters and the conjugated free fatty acids.

14. The process of claim 1, further comprising the steps
   (d) combining the reaction product with a 98% aqueous sulfuric acid solution in an amount of from about 1 to about 20 percent by weight to convert the potassium salts of conjugated fatty acids into conjugated free fatty acids; and
   (e) methylating the conjugated free fatty acids to generate a product comprising greater than about 95 percent by weight conjugated fatty acid methyl esters.

* * * * *